US00PP24272P2

(12) United States Plant Patent
Heuger

(10) Patent No.: US PP24,272 P2
(45) Date of Patent: Feb. 25, 2014

(54) ***HELLEBORUS* PLANT NAMED 'COSEH 960'**

(50) Latin Name: ***Helleborus niger*×*Helleborus hybridus***
Varietal Denomination: COSEH 960

(76) Inventor: Josef Heuger, Glandorf (DE)

( * ) Notice: Subject to any disclaimer, the term of this patent is extended or adjusted under 35 U.S.C. 154(b) by 75 days.

(21) Appl. No.: 13/506,699

(22) Filed: May 10, 2012

(51) Int. Cl.
*A01H 5/00* (2006.01)

(52) U.S. Cl.
USPC ..... Plt./439; Plt./263.1

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 960', characterized by its upright and mounded plant habit; uniform and freely flowering habit; dark green-colored leaves; long flowering period; single white-colored flowers; and good garden performance.

2 Drawing Sheets

Botanical designation: *Helleborus niger*×*Helleborus hybridus*.

Cultivar denomination: 'COSEH 960'.

BACKGROUND OF THE INVENTION

The present invention relates to a new and distinct cultivar of *Helleborus* plant, botanically known as *Helleborus niger*× *Helleborus hybridus*, and hereinafter referred to by the name 'COSEH 960'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2005 of an unnamed proprietary seedling selection of *Helleborus niger*, not patented, as the female, or seed, parent with an unnamed proprietary seedling selection of *Helleborus hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2008.

Asexual reproduction of the new *Helleborus* plant by divisions in a controlled greenhouse environment in Glandorf, Germany since March, 2008 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 960'.

These characteristics in combination distinguish 'COSEH 960' as a new and distinct *Helleborus* plant:

1. Upright and mounded plant habit.
2. Uniform and freely flowering habit.
3. Dark green-colored leaves.
4. Long flowering period.
5. Single white-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus hybridus* 'COSEH 710', disclosed in U.S. Plant Pat. No. 21,063. In side-by-side comparisons conducted in Glandorf, Germany, plants of the new *Helleborus* differed from plants of 'COSEH 710' in leaf and flower color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 960' grown in a container.

The photograph on the second sheet is a close-up view of a typical flower of 'COSEH 960'.

DETAILED BOTANICAL DESCRIPTION

The aforementioned photographs and following observations, measurements and values describe plants grown during the winter in 17-cm containers in a glass-covered greenhouse in Glandorf, Germany and under environmental conditions and cultural practices which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus hybridus* 'COSEH 960'.

Parentage:

*Female, or seed, parent.*—Unnamed proprietary seedling selection of *Helleborus niger*, not patented.

*Male, or pollen, parent.*—Unnamed proprietary seedling selection of *Helleborus hybridus*, not patented.

Propagation:

*Type.*—By tissue culture.

*Time to initiate roots, winter.*—About two months at 12° C.

*Time to produce a rooted young plant, winter.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and mounding plant habit with flowers held just above the foliar plane; plant shape is ovate; moderately vigorous growth habit.

*Plant height.*—About 47.6 cm.

*Plant diameter* (*area of spread*).—About 48.2 cm.

Foliage description:

*Arrangement.*—Leaves arranged in a basal rosette; leaves palmately compound with about seven leaflets per leaf

*Leaf length.*—About 20 cm.

*Leaf width.*—About 20.7 cm.

*Leaflet length.*—About 11.5 cm.

*Leaflet width.*—About 5.8 cm.

*Leaf shape.*—Palmate; orbicular in outline.

*Leaflet shape.*—Obovate.

*Leaflet apex.*—Broadly acute.

*Leaflet base.*—Cuneate.

*Leaflet margin.*—Sharply serrate; slightly undulate.

*Leaflet texture, upper and lower surfaces.*—Smooth, glabrous; leathery.

*Leaflet venation pattern.*—Pinnate.

*Leaflet color.*—Developing leaves, upper surface: Close to 137A. Developing leaves, lower surface: Close to 146B. Fully developed leaves, upper surface: Between 139A and 147A; venation, close to 144A to 144B, tinged at the base with close to N186C. Fully developed leaves, lower surface: Between 146B and 147B; venation, close to 181A.

*Petiole.*—Length: About 17.6 cm. Diameter: About 6 mm. Texture, upper and lower surfaces: Smooth, glabrous. Color, upper and lower surfaces: Close to 144A heavily dotted with close to N186C; at the base, close to 187C.

Flower description:

*Flower shape and habit.*—Single rotate flowers arranged in terminal and axillary cymes; freely and uniform flowering habit with about 16 flowers and flower buds developing per plant; flowers facing outwardly to nodding.

*Fragrance.*—None detected.

*Natural flowering season.*—Plants begin flowering about ten months after planting; long flowering period, plants flower from late winter to early spring in Germany.

*Flower longevity on the plant.*—About ten days; flowers not persistent.

*Flower buds.*—Length: About 1.5 cm. Diameter: About 1 cm. Shape: Ovate. Color: Close to 145C.

*Inflorescence height.*—About 10.7 cm.

*Inflorescence diameter.*—About 16.1 cm.

*Flower diameter.*—About 9 cm.

*Flower depth* (*height*).—About 2.5 cm.

*Petals.*—Transformed into nectaries.

*Sepals.*—Quantity and arrangement: Five arranged in a single whorl. Length: About 4.9 cm. Width: About 3.3 cm. Shape: Ovate to elliptic. Apex: Broadly acute to rounded. Base: Cuneate. Margin: Entire, undulate. Texture, upper and lower surfaces: Smooth, glabrous. Color: When opening, upper surface: Close to NN155B; base, close to 145B. When opening, lower surface: Close to NN155A; base, close to 145B. Fully opened, upper and lower surfaces: Close to NN155A; inconspicuous central band, close to 157C; base, close to 145B. With development, color becomes closer to 145A.

*Peduncles.*—Strength: Moderately strong. Length: About 35.3 cm. Diameter: About 5 mm. Aspect: About 10° from vertical. Texture: Smooth, glabrous. Color: Close to 144B to 144C slightly dotted with close to N186C.

*Pedicels.*—Strength: Moderately strong. Length: About 2 cm. Diameter: About 2 mm. Aspect: Erect to about 40° from the peduncle axis. Texture: Smooth, glabrous. Color: Close to 144C.

*Reproductive organs.*—Stamens: Quantity per flower: About 100. Filament length: About 2.1 cm. Filament color: Close to 155C. Anther shape: Reniform. Anther length: About 2 mm. Anther color: Close to 150C. Pollen amount: Scarce. Pollen color: Close to 4D. Pistils: Quantity per flower: About five to eight. Pistil length: About 1.4 cm. Stigma shape: Club-shaped. Stigma color: Close to 150D. Style length: About 1.3 cm. Style color: Close to 186C to 186D. Ovary color: Close to 145B. Nectaries (transformed petals): Quantity per flower: About 13. Length: About 1.2 cm. Diameter: About 3.5 mm. Shape: Narrow triangular, flattened tubular. Color: Close to 144C.

*Seeds and fruits.*—Seed and fruit development have not been observed on plants of the new *Helleborus*.

Garden performance: Plants of the new *Helleborus* have been observed to have good garden performance and to tolerate rain and wind; plants of the new *Helleborus* have been observed to tolerate high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 960' as illustrated and described.

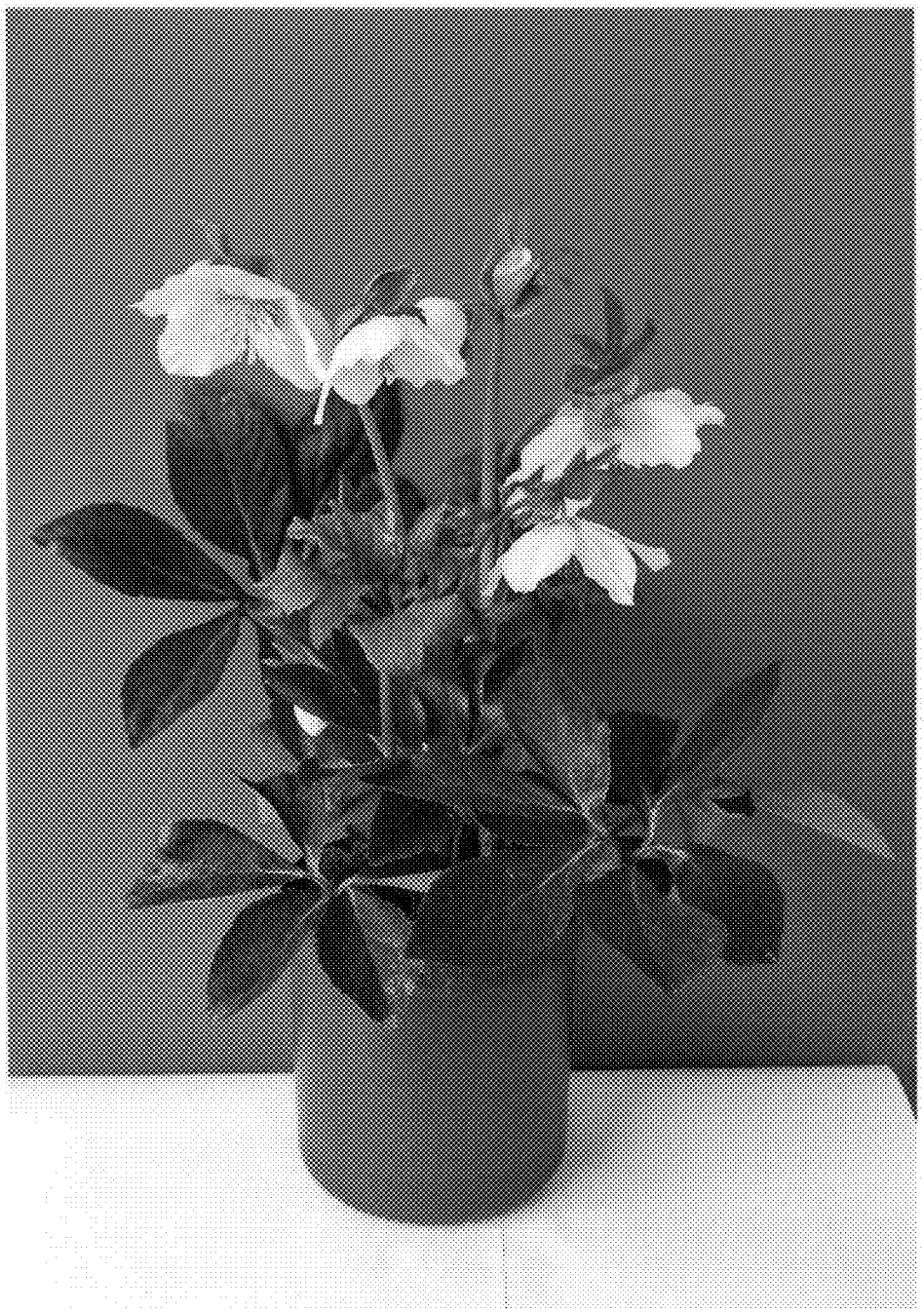

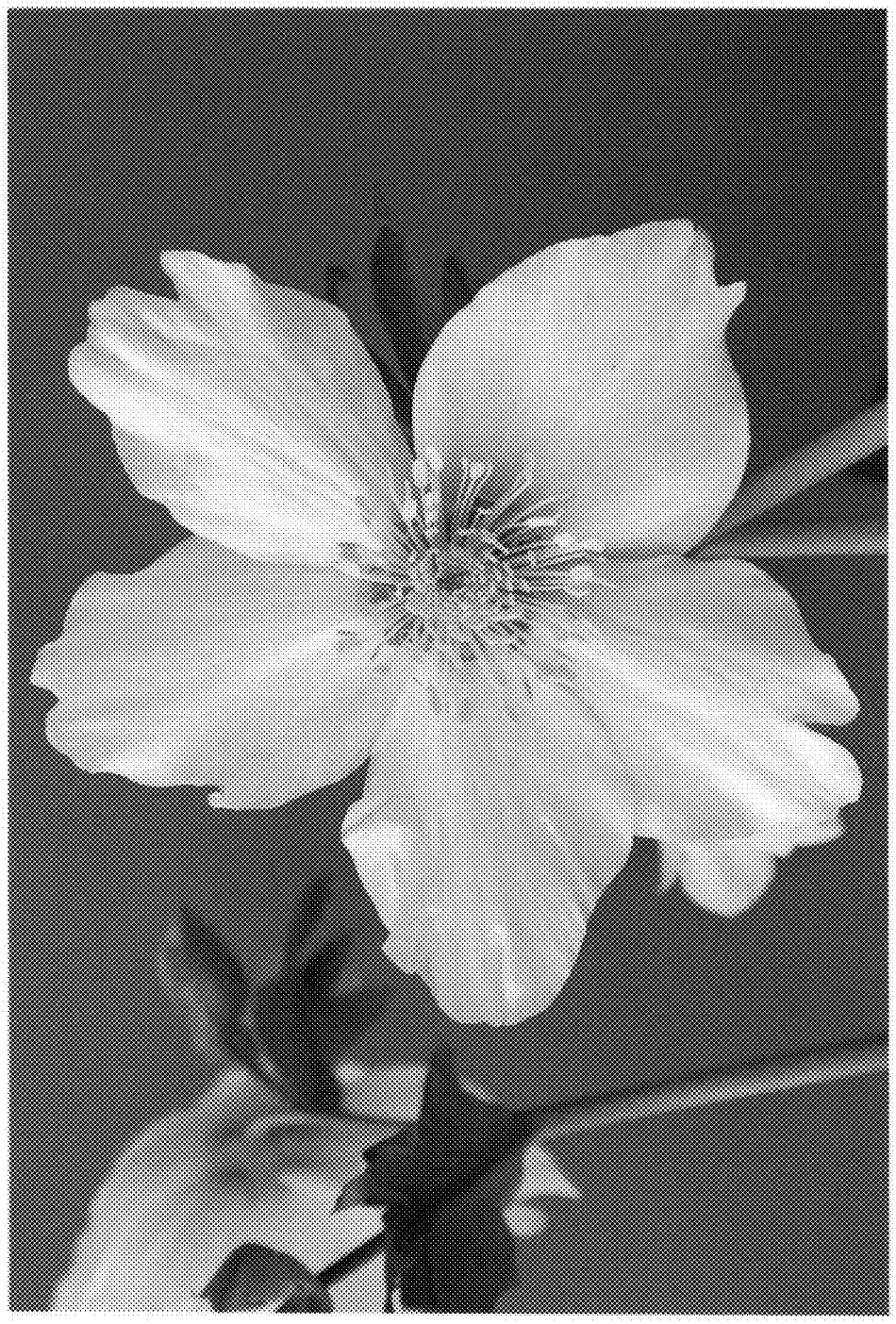

* * * * *